United States Patent [19]
Anthony

[11] Patent Number: 5,287,423
[45] Date of Patent: Feb. 15, 1994

[54] MULTIPLEXER FOR USE WITH A DEVICE FOR OPTICALLY ANALYZING A SAMPLE

[75] Inventor: Michael Anthony, Gaithersburg, Md.

[73] Assignee: L. T. Industries, Inc., Rockville, Md.

[21] Appl. No.: 647,631

[22] Filed: Jan. 31, 1991

[51] Int. Cl.⁵ .......................... G02B 6/36; G02B 7/26
[52] U.S. Cl. .............................................. 385/26
[58] Field of Search ............... 350/96.20, 96.21, 96.22; 385/26

[56] References Cited

U.S. PATENT DOCUMENTS

| | | | |
|---|---|---|---|
| 3,350,156 | 3/1964 | Adams | 350/202 |
| 4,436,367 | 3/1984 | Lewis et al. | 350/96.20 |
| 4,525,025 | 6/1985 | Hohmann et al. | 350/96.20 |
| 4,540,282 | 9/1985 | Landa et al. | 356/328 |
| 4,594,533 | 6/1986 | Snook et al. | 315/363 |
| 4,626,065 | 12/1986 | Mori | 350/96.15 |
| 4,630,255 | 12/1986 | Gouali et al. | 370/3 |
| 4,636,028 | 1/1987 | Mori | 350/96.15 |
| 4,669,766 | 6/1987 | Mori | 350/96.15 |
| 4,699,766 | 10/1987 | Yamashita | 422/64 |
| 4,744,617 | 5/1988 | Hvezda et al. | 350/96.15 |
| 4,767,175 | 8/1988 | Böhner et al. | 350/96.20 |
| 4,834,484 | 5/1989 | Gorman et al. | 385/26 |
| 4,848,871 | 7/1989 | Seidel et al. | 350/96.29 |
| 4,898,447 | 2/1990 | Kuhlmann | 350/96.20 |
| 4,900,117 | 2/1990 | Chen | 350/96.20 |
| 4,989,932 | 2/1991 | Landa et al. | 356/328 |

Primary Examiner—Rodney B. Bovernick
Assistant Examiner—Robert E. Wise
Attorney, Agent, or Firm—Sterne, Kessler, Goldstein & Fox

[57] ABSTRACT

The present invention is a multiplexer for use with an apparatus for optically analyzing a sample. This multiplexer includes a body portion having a primary inlet port. The light received through the light inlet port is sent through a first fiber optic bundle which may be rotated by a fiber carriage to any of several outlet fiber couplers which may be connected to various samples. A position optical sensor assures proper alignment between the first fiber optic bundle and the fiber couplers by sensing the position of a chopper disc which is mounted to the rotating fiber carriage. Once light is passed through the sample, it is passed back into the multiplexer through inlet fiber couplers. These additional fiber couplers are linked to a second fiber optic bundle leading to a detector fiber coupler which may be connected to a fixed fiber cable.

7 Claims, 3 Drawing Sheets

MULTIPLEXER FOR USE WITH A DEVICE FOR OPTICALLY ANALYZING A SAMPLE

BACKGROUND OF THE INVENTION

1. Field of the Invention

The present invention relates generally to a multiplexer which enables a plurality of samples to be analyzed using spectral analysis.

2. Background

U.S. Pat. No. 4,540,282 to Landa et al. (the Landa patent) is an apparatus for optically analyzing a sample. The device described by the Landa patent is an electro-optical system for rapid, accurate spectral analysis of the reflectivity and/or transmissivity of samples. In this device, a holographic diffraction grating is oscillated at high speeds to provide a rapid scanning of monochromatic light through a spectrum of wavelengths. The grating drive is an electrically driven mechanical oscillator which utilizes the back EMF of the oscillator motor to maintain oscillation at a desired amplitude and frequency. An optical shutter alternately blocks the light as the grating is oscillated.

In particular, a device as described by the Landa patent may be used to analyze light which has passed through a sample using, for example, a probe. U.S. patent application Ser. No. 07/318,245, now U.S. Pat. No. 5,044,755 to Landa et al. (the Landa patent application) discloses probes which may be used for this purpose.

The present invention is a device which may be used in conjunction with the device described by the Landa patent (or similar device) to increase the productivity thereof and to eliminate the need for multiple optical analyzing devices.

It is one object of the invention to provide a multiplexer which allows several samples to be analyzed substantially simultaneously.

It is another object of the invention to provide a multiplexer which minimizes misalignment between output/input ports and internal optical elements.

It is yet another object of the invention to provide a multiplexer which greatly reduces internal optical loss.

It is yet another object of the invention to provide a multiplexer which facilitates path referencing.

It is yet another object of the invention to provide a multiplexer which is small and compact in size, yet easy to manufacture.

It is yet another object of the invention to provide a multiplexer which may be used in a remote location.

SUMMARY OF THE INVENTION

In accordance with the purposes of the present invention, as embodied and described herein, the present invention is a multiplexer for use with an apparatus for optically analyzing a sample. This multiplexer includes a body portion having a primary light inlet port. The light received through the light inlet port is sent through a first fiber optic bundle which may be rotated by a fiber carriage to any one of several output fiber couplers which delivers light to various samples. A position optical sensor assures proper alignment between the first optic bundle and the fiber couplers by sensing the position of a chopper disc which is fastened to the rotating fiber carriage. The light then passes through a sample and may be passed back through the multiplexer through an additional fiber coupler. This additional fiber coupler may be one of several which are linked to a second fiber optic bundle leading to a detector fiber coupler. This detector fiber coupler may be connected to a fixed fiber cable for transmitting the light to a detecting device for analysis.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE PREFERRED EMBODIMENTS

Figure 1:
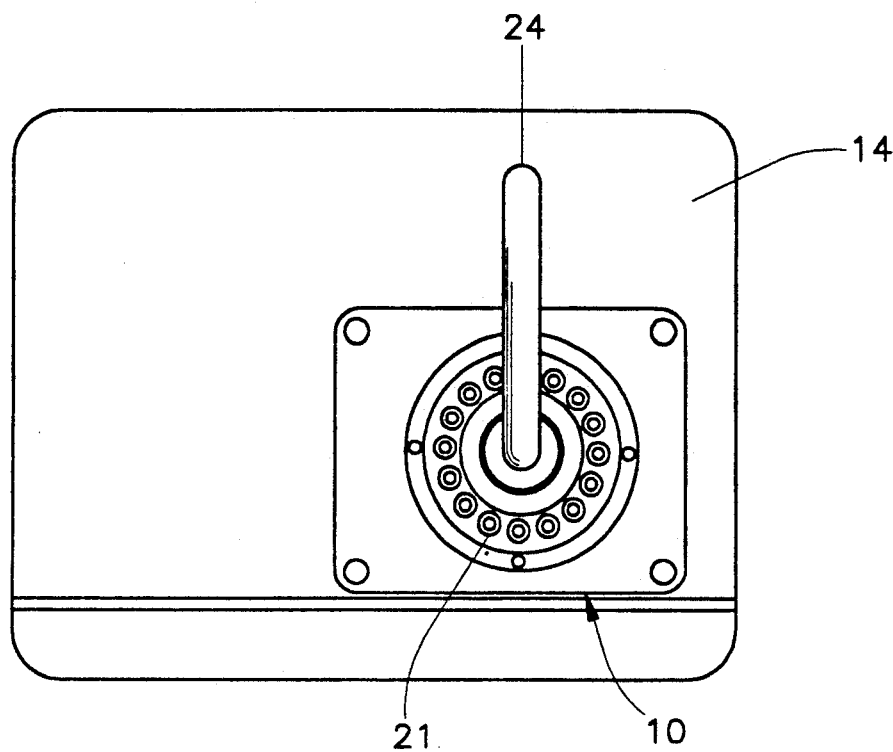
FIG. 1 is a front view of the multiplexer of the instant invention mounted on a face plate.

The present invention is a multiplexer for use with an apparatus for optically analyzing a sample, such as the device disclosed in U.S. Pat. No. 4,540,282 to Landa et al. (the Landa patent). The disclosure of the Landa patent is herein incorporated by reference and forms a part of the specification.

The device which is described by the Landa patent is one device which may be used with this multiplexer. However, one of ordinary skill in the art will appreciate that other devices for optically analyzing a sample may be used in conjunction with the multiplexer of the instant invention.

The Landa patent describes an electro-optical system which determines the reflectivity and/or transmissivity of samples. In order to spectrally analyze a sample, a light dispersing element such as a holographic diffraction grating is sinusoidally oscillated at a preselected high speed to provide a rapid scanning of monochromatic light through a selected spectrum of wavelengths. Light which is downstream of the diffraction grating passes through an exit slit which may be adjustable to enable selection of an optimal spectral bandwidth for a particular application. Light passing through such an exit slit may then be passed to the multiplexer of the present invention.

Referring now to the present invention, the multiplexer shown generally as 10 includes a body portion or housing 12 which may be cylindrically shaped. The multiplexer may be mounted on a bracket plate 11 and face plate 14. Light is introduced into the multiplexer 10 via a primary inlet port 16 and through receiving optics 17. Light from the electro-optical system of the Landa patent passes through primary inlet port 16. The light then travels through a first fiber optic bundle 18 to any one of a series of fiber couplers 21. Fiber couplers 21, which may be circularly arranged on the end of a rotating fiber carriage 30, act as output and/or input ports. After passing through one of fiber couplers 21, the light is transmitted through additional fiber optic bundles or the like to a sample.

Figure 2:
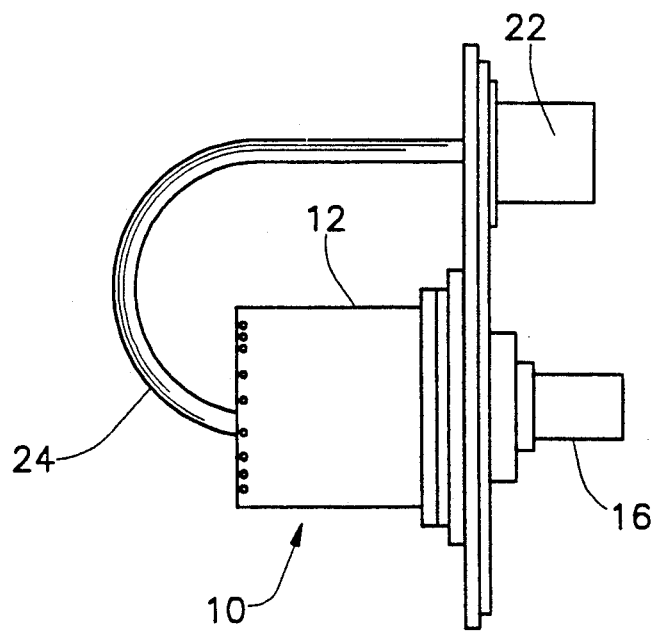
FIG. 2 is a side view of the multiplexer of the instant invention mounted on a face plate and coupled to an externally mounted detector.
Figure 3:
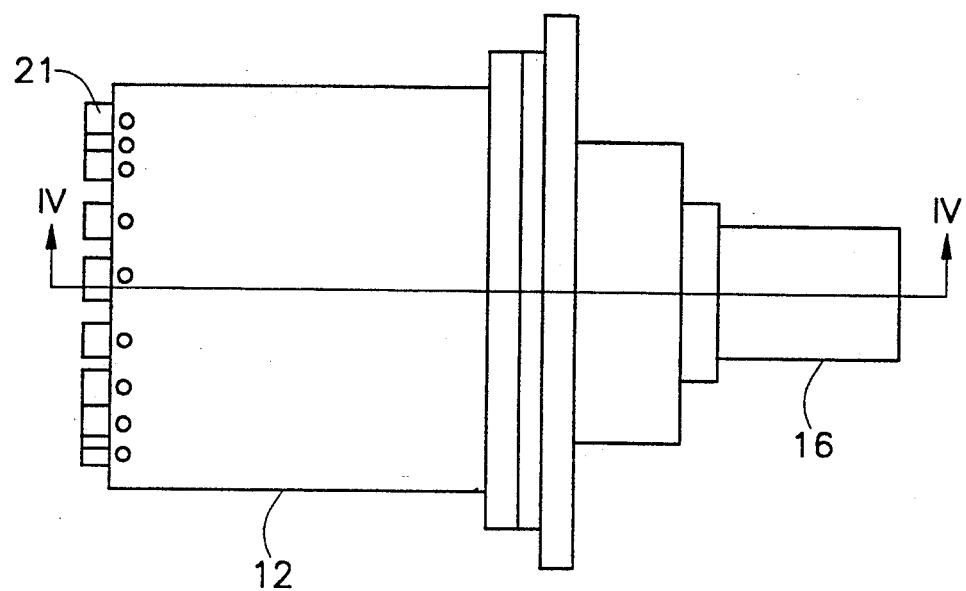
FIG. 3 is a side view of the multiplexer of the instant invention.

There are three modes in which a device of the type described by the Landa patent may operate. In the first mode, the light passes through the fiber optic bundle and through a probe which may be in light communication with the sample. In this mode, the reflectance mode, light reflects from the sample, back into the probe and through the fiber optic bundle. A bidirectional fiber optics configuration is used to allow light to pass through the fiber optic bundle in both directions simultaneously. The light is then either passed to an external detector/analyzer 22 (FIG. 2) or may be passed back through a second fiber coupler 21 in the multiplexer.

The second mode of operation is the transmittance mode. In this mode, light passes through fiber optic bundles through a probe which transmits light through a sample. The light in this mode is then either passed directly to an external detector/analyzer 22 or may be passed through a second fiber coupler 21 in the multiplexer.

In the third mode of operation, the transflectance mode, light passes through a fiber optics bundle to a probe. Part of the light emanating from the probe will be reflected back through the probe and through the fiber optics bundle. The remaining light will be transmitted through the sample and reflected back through the sample via a mirror or other means for reflecting light. This reflected light will pass through the sample and again pass through the probe and through the fiber optics bundle to be analyzed. Both the light which is reflected from the sample and transmitted through the sample will then either pass directly to an external detector/analyzer 22 or may be passed through a second fiber coupler 21 in the multiplexer. U.S. patent application Ser. No. 07/318,245 now U.S. Pat. No. 5,044,755 Landa et al. (the Landa application) discloses probes which utilize the aforementioned reflectance, transmittance, and transflectance modes. The disclosure of the Landa application is herein incorporated by reference and forms a part of this specification.

Figure 4:
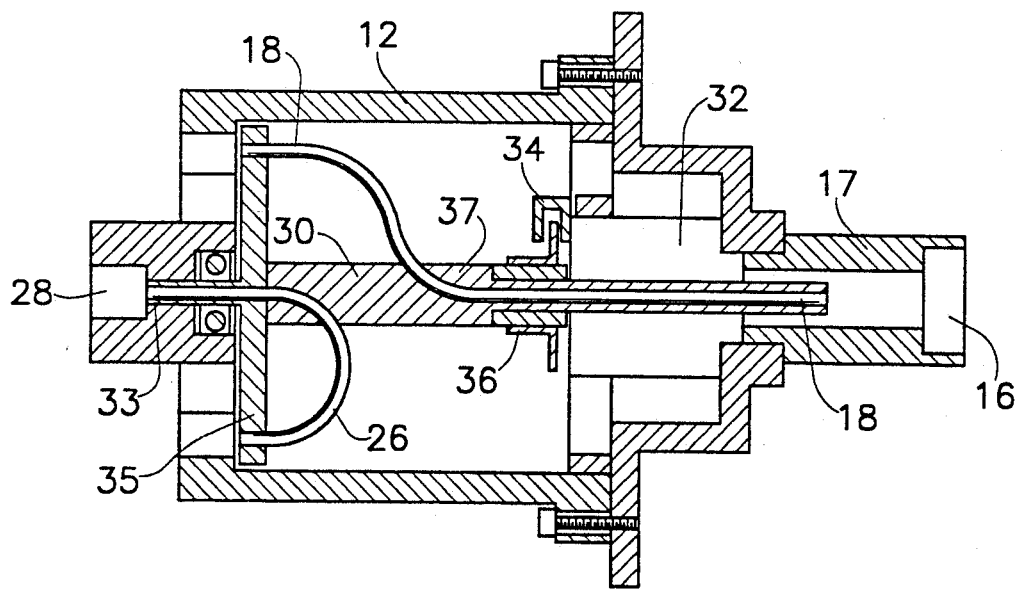
FIG. 4 is a sectional view of the multiplexer of the instant invention taken along line IV—IV of FIG. 3.

Referring now to FIG. 4, regardless of the mode of operation of the fiber optics and probe, the multiplexer of the present invention operates in the same way. Whether the device is operating in a reflectance mode, a transmittance mode, or a transflectance mode, the light from the inlet port 16 and first fiber optic bundle 18 leaves the multiplexer 10 through a fiber coupler 21 which serves as the outlet, and passes through a sample. The light may return to a second fiber coupler 21. Once light passes through a sample, and back through a second fiber coupler 21 which serves as an inlet, the light passes through a second fiber optic bundle 26 to a fixed fiber cable 24 (FIG. 2) leading to a detector/analyzer 22 which may be externally mounted to face plate 14. Fixed fiber cable 24 is connected to multiplexer 10 via a detector fiber coupler 28. Fiber couplers 21 may be circularly arranged with the outlet fiber couplers extending along one-half of the circular perimeter and the inlet fiber couplers 21 extending along the opposite half of the circular perimeter.

In the alternative (not shown), after having passed through a sample, light may be sent via a similar fixed fiber cable directly from the sample to a detector/analyzer, bypassing the second fiber optic bundle. The light sent by the fixed fiber cable is then optically analyzed by detector/analyzer such as the device described in the Landa patent.

The construction of the present invention enables multiplexing, the sampling of a number of different products, substantially simultaneously. This possible because of the rotating fiber carriage 30 which rotates about the longitudinal axis of the body portion 12 of multiplexer 10. As seen in FIG. 4, both first and second fiber optic bundles 18 and 26 have portions which are disposed along the center axis of the rotating fiber carriage 30. Rotating fiber carriage 30 includes an end piece 33 which may be aligned with fiber couplers 21. In addition, end piece 33 is aligned with detector fiber coupler 28 regardless of the orientation of end piece 33 relative the fiber couplers 21. The end piece 33 of the carriage 30 includes a disc 35. The carriage 30 also includes a shaft 37 which may be the output shaft of a stepper motor 32. Each end of both the first and second fiber optic bundles 18 and 26 are fixed relative the rotating fiber carriage 30. Thus, both the first and second fiber optic bundles 18 and 26 rotate with the rotating fiber carriage 30.

Figure 5:
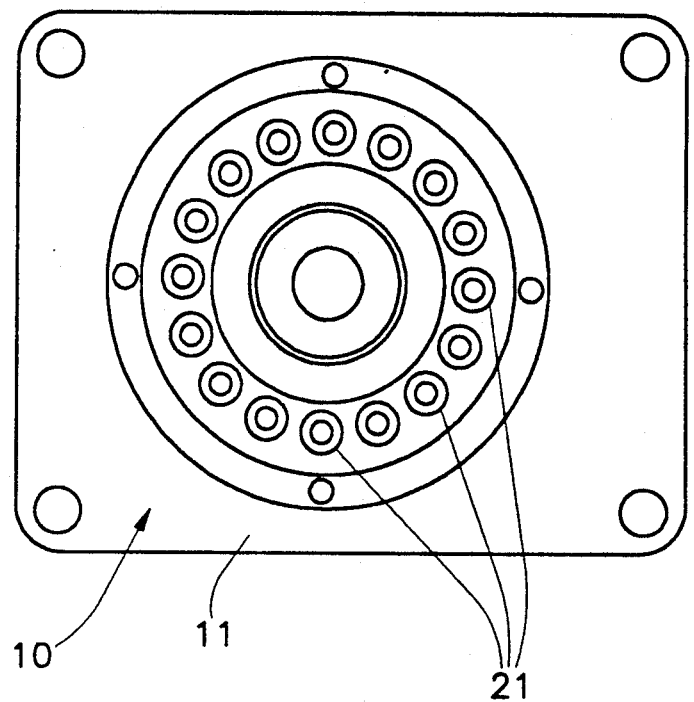
FIG. 5 is a front view of the multiplexer of the instant invention.

As seen in FIG. 4, light passes through first fiber optic bundle 18, exits through one coupler of fiber couplers 21 and returns to the multiplexer via a second coupler of fiber couplers 21 leading to a second fiber optic bundle 26. However, it can be seen that by rotating fiber carriage 30, which causes both the first and second fiber optic bundles 18 and 26 to also rotate, light would exit a third coupler of fiber couplers 21 and would return to the multiplexer via a fourth coupler of fiber couplers 21, again leading to second fiber optic bundle 26. While the embodiment shown in FIG. 5 shows 16 fiber couplers (8 pairs of fiber couplers), it is contemplated that any number of couplers 21 may be used to practice the invention. Having passed through second fiber optic bundle 26, light would exit the multiplexer via fixed fiber cable 24 which is mounted to the multiplexer 10 via detector fiber coupler 28.

To practice the invention, stepper motor 32 may be attached to rotating fiber carriage 30. This stepper motor 32 can access each pair of fiber couplers 21 randomly and may idle on each set of fiber couplers 21 according to the requirements of the user. In order to accomplish such a result, conventional electronics and software may be used.

In order for the stepper motor 32 to stop at the exact necessary position, a position optical sensor 34 mounted within multiplexer 10 and a chopper disc 36 mounted on the rotating fiber carriage 30 may be used. Position optical sensor 34 or the like may be used to emit a light signal. When the light of the optical sensor passes through small holes (not shown) on chopper disc 36, a signal can be relayed to the motor 32 so that the motor will stop at an exact point. Although the holes in chopper disc 36 are preferably only about 20 millimeters in diameter, the hole may nevertheless be too large for the rotating fiber carriage 30 to stop at precisely the proper point for the proper alignment of both first and second fiber optical bundles 18 and 26 and fiber couplers 21. In order to alleviate this problem, it may be necessary to control the motor by looking for the point at which the light intensity through the hole is the maximum. The light intensity passing through the hole will be parabolic in profile. By finding the point at which the intensity is greatest, it is possible to stop the motor at precisely, or nearly precisely the proper point so that the light passing from or to fiber optic bundles 18 and 26, and the fiber couplers 21 will be in proper alignment. The first step in determining proper alignment may require calibration of the profiles of the light intensity of the position optical sensor 34. Of course, one of ordinary skill in the art will appreciate that there are other available techniques to assure proper alignment of both first and second fiber optic bundles 18 and 26, and fiber couplers 21.

One of the great advantages of the multiplexer 10 is that it permits the sampling of a number of different products substantially simultaneously as rotating fiber carriage 30 may be rotated at very fast speeds (2 revolutions per second). In addition, because the rotating fiber carriage 30 and end piece 33 are inherently concentric with fiber couplers 21, misalignment of the couplers 21 with the rotating fiber bundles is minimized. As one of ordinary skill in the art will appreciate, by envisioning body 12 in a cylindrical coordinate system (r,θ,z), both the radial (r) and longitudinal (z) coordinates remain constant throughout the multiplexing procedure thereby providing an inherently aligned configuration. The only variable component, the angular coordinate (θ), is regulated via position optical sensor 34 and chopper disc 36, thereby minimizing the potential for misalignment of the fiber couplers 21 with rotating fiber bundles 18 and 26.

Furthermore, because the multiplexer utilizes fiber optic bundles 18 and 26, the potential for optical loss within the multiplexer is greatly reduced. In addition, the aforementioned preferred embodiment is ideal for remote location as it requires a single inlet element 16 and a single return element 28.

Yet another advantage of the multiplexer 10 is that path referencing is greatly facilitated. By rotating disc 35 so that first fiber optic bundle 18 is aligned with an inlet coupler 21 and second fiber optic bundle 26 is aligned with an outlet coupler 21, light travels through the sample in the opposite direction. Thus, in this mode of operation, a cable/ light path (not shown) normally used to transmit light from the sample to an inlet coupler would now be used to transmit light from the same inlet coupler to the sample. This technique allows the user who is positioned at the sample location to determine whether the transmission of light through that particular cable/ light path is impeded in any way.

The embodiment was chosen and described in order to best explain the principles of the invention and its practical application to thereby enable others skilled in the art to best utilize the invention. For example, the multiplexer of the present invention has been described with particular reference to multiplexer light to be used to analyze samples with an electro optical device; however, the concepts of the invention could be adapted to other technologies such as those technologies found in the communications field. In addition, while the preferred embodiment has been described with a series of outlet fiber couplers 21 extending along one-half a circular perimeter and a series of inlet fiber couplers 21 extending along the opposite half of the circular perimeter, one of ordinary skill in the art will appreciate that a variety of configurations of inlet/ outlet fiber couplers is possible; for example, the inlet/outlet fiber couplers may be staggered one after another. It is intended that the scope of the invention be defined by the claims appended hereto.

The foregoing description of the preferred embodiment of the invention has been presented for purposes of illustration and description. It is not intended to be exhaustive or limited to the precise form disclosed. Obviously, many modifications and variations may be made in light of the above teachings.

What is claimed is:

1. A multiplexer for introducing light to multiple samples, comprising:
   a cylindrical multiplexer housing;
   a carriage concentrically disposed within said housing, said carriage having a shaft portion and a disc portion disposed at one end of said shaft portion;
   a stepper motor for rotating said shaft portion;
   a fiber optic cable wherein a first end of said cable is substantially concentric with said shaft portion and wherein a second end is attached to said disc portion at a location a finite distance from the center of said disc;
   means for detecting the position of said shaft relative to said housing; and
   a plurality of outlets disposed on at least one end of said housing;
   whereby said stepper motor rotates said carriage and said fiber optic cable to permit the selective serial transmission of light through said fiber optic cable to said outlets.

2. The multiplexer of claim 1 further comprising a series of inlets disposed on at least one end of said housing.

3. The multiplexer of claim 2 further comprising a second fiber optic cable at least partially extending through said disc portion of said carriage, wherein both ends of said second cable are attached to said disc portion of said carriage, whereby said second cable receives light from said inlets.

4. A multiplexer for introducing light to multiple samples, comprising:
   a multiplexer housing,
   a first means for transmitting light,
   means for rotating said first means for transmitting light, wherein said first means for transmitting light is fixed relative to said means for rotating,
   a plurality of outlets disposed on said housing,
   a plurality of inlets disposed on said housing,
   so that light is selectively transmitted through said outlets and said inlets.

5. Them multiplexer of claim 4, wherein said first means for transmitting light comprises a fiber optic cable.

6. The multiplexer of claim 4 wherein said means for rotating comprises a rotating fiber carriage.

7. The multiplexer of claim 4 further comprising a second means for transmitting light.

* * * * *